United States Patent [19]

Hensen et al.

[11] Patent Number: 4,744,977
[45] Date of Patent: May 17, 1988

[54] QUATERNARY AMMONIUM COMPOUND HAIR CONDITIONERS

[75] Inventors: Hermann Hensen, Hilden; Horst Rutzen, Langenfeld; Peter Busch, Erkrath-Unterbach; Dagmar Stuhrmann, Duesseldorf; Klaus Thiele, Langenfeld, all of Fed. Rep. of Germany

[73] Assignee: Henkel Kommanditgesellschaft auf Aktien, Duesseldorf, Fed. Rep. of Germany

[21] Appl. No.: 798,201

[22] Filed: Nov. 14, 1985

[30] Foreign Application Priority Data

Nov. 17, 1984 [DE] Fed. Rep. of Germany ....... 3442175

[51] Int. Cl.⁴ .................... A61K 7/06; A61K 7/08; A61K 7/11
[52] U.S. Cl. .................... 424/70; 424/DIG. 1; 424/DIG. 2; 424/DIG. 4; 424/47; 424/71; 424/72; 514/783; 514/880; 514/881; 514/904
[58] Field of Search ........................... 424/70

[56] References Cited

U.S. PATENT DOCUMENTS

| | | | |
|---|---|---|---|
| 3,962,418 | 6/1976 | Birkofer | 424/70 |
| 4,492,802 | 1/1985 | Rutzen et al. | 564/292 |

FOREIGN PATENT DOCUMENTS

| | | | |
|---|---|---|---|
| 2324290 | 4/1970 | France | 424/70 |
| 2349646 | 11/1977 | France | 424/70 |
| 2432309 | 2/1980 | France | 424/70 |

OTHER PUBLICATIONS

Riechstoffe, Aromen, Kosmetika, No. 12, (1977), p. 325, columns 2 and 3.
Chemical Abstract 93:31628K, 1984.
Chemical Abstract 88:39247c, 1979.
Chemical Abstract 86:157447z, 1977.
Chemical Abstracts, 1975, vol. 84,(2), p. 8851h.
Chemical Abstracts, 1976, vol. 85,(10), p. 68131d.
Chemical Abstracts, 1977, vol. 86,(22), pp. 157446y, 157444w, 157445x, 157447z.
Chemical Abstracts, 1979, vol. 90,(16), p. 127401v.
Chemical Abstracts, 1984, vol. 101,(1), p. 6603z.
Chemical Abstracts, 1984, vol. 101,(9), p. 72259t.
Sagarin, Cosmetics Science and Technology, 1957, pp. 1029 and 1030.

*Primary Examiner*—Dale R. Ore
*Attorney, Agent, or Firm*—Ernest G. Szoke; Henry E. Millson, Jr.; Mark A. Greenfield

[57] ABSTRACT

A hair care preparation containing a hair conditioning effective amount of a compound of the formula:

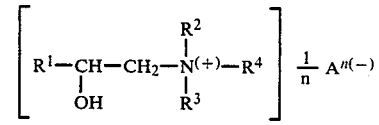

wherein:
$R^1$ is a $C_{12\text{-}16}$-n-alkyl;
$R^2$ is a $C_{1\text{-}4}$-n-alkyl;
is a $C_{1\text{-}4}$-hydroxyalkyl;
$R^4$ is a $C_{1\text{-}4}$-n-alkyl or a $C_{2\text{-}4}$-hydroxyalkyl;
A is an inorganic or organic acid anion; and
n is the valence of said anion.

16 Claims, No Drawings

QUATERNARY AMMONIUM COMPOUND HAIR CONDITIONERS

BACKGROUND OF THE INVENTION

1. Field of the Invention

This invention relates to hair care preparations containing certain quaternary ammonium compounds which exhibit effective hair conditioning and processing properties, and methods for the use of such preparations.

2. Statement of the Related Art

Cationic surfactants, particularly quaternary ammonium compounds, are used in hair care as revitalizing and conditioning components for improving the combability, body and feel of the hair and for reducing its static chargeability. Such products are generally used in hair aftertreatment preparations which, after shampooing, are intended to restore favorable trichocosmetic properties to the hair. However, they are not suitable as additives to shampoos for obtaining a conditioning effect at the same time as the hair is washed. This is because most known quaternary ammonium compounds are incompatible with the high-foam anionic surfactants normally used in shampoos in the concentrations required for an adequate conditioning effect and, instead, form sparingly water-soluble, cosmetically inactive deposits. Quaternary ammonium compounds which are more compatible with anionic surfactants generally have an unsatisfactory conditioning effect.

Although water soluble cationic polymers are generally compatible with anionic surfactants, they have other disadvantages, for example accumulation on the hair after repeated treatment and inadequate prevention of the static charging of dry hair.

It has therefore become most desireable to provide quaternary ammonium compounds which have strong revitalizing and conditioning properties on human hair and which may even be incorporated in hair care preparations, especially in shampoos based on high-foam anionic surfactants in concentrations sufficient for a satisfactory cosmetic effect without causing any clouding or precipitation.

DESCRIPTION OF THE INVENTION

It has been found that hair care preparations containg quaternary ammonium compounds corresponding to the general formula:

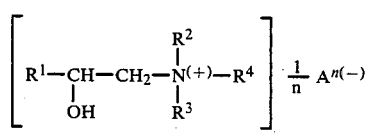

wherein $R^1$ is a $C_{12\text{-}16}$-n-alkyl, $R^2$ is a $C_{1\text{-}4}$-n-alkyl, $R^3$ is a $C_{1\text{-}4}$-hydroxyalkyl, and $R^4$ is a $C_{1\text{-}4}$-n-alkyl or a $C_{2\text{-}4}$-hydroxyalkyl, A is an inorganic or organic acid anion and n is the anion's valence: have strong revitalizing and conditioning properties on human hair. The quanternary ammonium compounds corresponding to general formula I are known. Their production from epoxy alkanes corresponding to the general formula

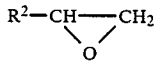

and tertiary amine salts corresponding to the formula

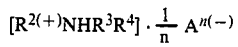

in which $R^1$, $R^2$, $R^3$, $R^4$ and n have the same definitions as in general formula I, is described in U.S. Pat. No. 4,492,802 which is incorporated herein by reference and in corresponding published German application 31 16 087. U.S. Pat. No. b 4,492,802 states that the compounds disclosed therein are useful as textile softeners and antistats, and as antibacterial agents for food containers. It also is disclosed that they may be incorporated in textile detergent formulations containing nonionic surfactants.

Compounds of formula I in which $R^2$ is methyl, $R^3$ is 2-hydroxyethyl, $R^4$ is methyl or 2-hydroxyethyl, and A is a chloride ion are particularly suitable for producing hair care preparations according to the invention. These compounds show particularly favorable activity in improving the combability of hair and in preventing static charging. They may be used in hair-care preparations generally in conditioning effective amounts, especially in quantities of from 0.1 to 15% by weight. All percentages herein are based upon the weight of the total formulation, unless indicated otherwise.

In addition, the quaternary ammonium compounds of general formula I are distinguished by special processing properties which unexpectedly make them particularly suitable as a conditioning component in hair care preparations. Aqueous solutions containing from 0.5 to 15% by weight of the quaternary ammonium compounds may be increased in viscosity by the addition of simple electrolytes. In this way, it is possible to prepare clear, aqueous, hair care preparations, such as hair rinses and to adjust them to a suitable viscosity for application to hair without the need for polymeric thickeners, merely by additions of from 0.1 to 10% by weight of at least one simple salt from the group comprising chlorides, bromides, sulfates, carbonates and/or phosphates of lithium, sodium, potassium or magnesium. Solutions having structural viscosity are obtained which appear more highly viscous at rest than during viscosity measurement in the presence of shear forces, thus making the preparations easy to apply but retaining desireable properties once on the hair.

Another advantage of the quaternary ammonium compounds of general formula I in processing terms is their high compatibility with anionic surfactants, particularly with the high foaming alkali, ammonium, magnesium, mono-, di- and triethanolammonium salts of anionic surfactants containing an optionally ethoxylated linear $C_{10\text{-}18}$-alkyl moiety and a sulfate or sulfonate moiety in the molecule. Examples of anionic surfactants containing these characteristic structural elements are $C_{10\text{-}16}$-alkyl sulfates, $C_{12\text{-}16}$-alkyl ether sulfates containing from 1 to 12 glycol ether groups, $C_{10\text{-}18}$ alkane sulfonates, alkene and hydroxyalkane sulfonates obtained by the sulfonation of $C_{10\text{-}18}$-$\alpha$-olefins, fatty acid alkylolamide and fatty acid alkylolamide polyglycol ether sulfates, fatty acid monoglyceride sulfates, sulfosuccinic acid monoalkyl esters, acyl taurides and $C_{10\text{-}18}$-acyl isethionates. These anionic surfactants have the formula $R^5$—$O(C_2H_4O)_m$—$SO_3M$ wherein: $R^5$ is a linear $C_{10\text{-}18}$- alkyl; m is 0 or an integer from 1 to 12; and M is lithium, sodium, potassium, magnesium, ammonium, monoethanolammonium, diethanolammonium, or triethanolammonium. Hair care preparations containing anionic surfactants of this type may contain quaternary ammonium compounds of general formula I dissolved in a quantity of up to 50% by weight of the anionic surfactant, and are clear and without clouding or deposit formation.

Fatty alcohol sulfates and fatty alcohol ether sulfates are particularly suitable for the production of shampoos. One preferred embodiment of the invention is a hair care preparation in the form of a shampoo whose critical ingredients comprise:

0.5 to 8% by weight of at least one quaternary ammonium compound corresponding to general formula I and 5 to 20% by weight of at least one anionic surfactant of the formula: $R^5—O(C_2H_4O)_m—SO_3M$, in which $R^5$ is a linear $C_{10-16}$-alkyl, m=0 or a number of from 1 to 12 and M is a lithium, sodium, potassium, ammonium, magnesium, mono-, di- or triethanolammonium ion, in addition to other standard components of shampoos, including surfactants of different ionicity. It is particularly preferred to use a surfactant combination in which the anionic surfactant is substituted up to 50% by weight by an ampholytic or zwitterionic surfactant or a mixture thereof. Suitable ampholytic surfactants are N-($C_{8-18}$)-alkyl-$\beta$-aminopropionic acids or N-hydroxyethyl-N-cocosacylamidopropyl glycine. Suitable zwitterionic surfactants (betaine surfactants) are N-cocosalkyldimethyl glycine or N-cocosacylamidopropyl dimethyl glycine.

Nonionic surfactants may also be present in small quantities in shampoos according to the invention, although they are not preferred. Suitable nonionic surfactants are adducts of from 6 to 20 mols of ethylene oxide with $C_{12-18}$-fatty alcohols, with $C_{12-18}$-fatty acids, with $C_{8-12}$-alkyl phenols, with fatty acid alkylolamides, with fatty acid mono- and diglycerides or with sorbitan fatty acid esters. Other suitable nonionic surfactants are fatty acid mono- and diethanolamides and amine oxide surfactants.

In addition, the shampoos according to the invention may contain at least one standard additive such as: thickeners of the fatty acid alkylolamide or polyvinyl pyrrolidone type; opacifiers such as ethylene glycol distearate; pH stabilizers (buffers) such as alkali or ammonium phosphates or citrates; preservatives such as formaldehyde, p-hydroxybenzoic acid esters; dyes for the shampoo itself; perfumes; and also standard trichocosmetic components such as antidandruff agents such as selenium compounds, sebostatics, vitamins, vegetable extracts, and the like.

Hair rinsing preparations, used independently of shampoos, represent another preferred embodiment of the invention. Conditioning hair rinsing preparations are normally formulated as oil-in-water emulsions of fatty components (for example cetyl alcohol and/or stearyl alcohol) in water with the aid of nonionic emulsifiers and protective colloids. The conditioning components used are quaternary ammonium compounds. Hair rinsing preparations for use on wet hair after shampooing according to the invention may be formulated as clear, aqueous solutions containing, as critical ingredients:

0.5 to 10% by weight of at least one quaternary ammonium compound corresponding to general formula I and 0.1 to 10% by weight of an aqueous solution of at least one simple salt from the group comprising chlorides, bromides, sulfates, carbonates and/or phosphates of lithium, sodium, potassium, ammonium or magnesium.

Sodium chloride or magnesium chloride is preferably used as the electrolyte for thickening preparations such as these.

In addition to the critical constituents, the hair-rinsing preparations according to the invention may contain standard auxiliaries such as dyes, perfumes, preservatives and trichocosmetic components such as antidandruff agents, sebostatics, vitamins, vegetable extracts, and the like.

Hair aftertreatment preparations according to the invention which remain on the hair after application, such as setting lotions, wave-sets, and blow-wave preperations, critically contain at least one compound according to general formula I, and preferably contain lower alcohols, particularly ethanol and/or isopropanol, in the normally used quantities of from 10 to 50%. Setting lotions and blow-wave preparations additionally contain hair-setting anionic and/or nonionic film-forming polymers such as polyvinyl pyrrolidones or copolymers of maleic acid and acrylates or methacrylates, in quantities of from 0.1 to 1.0% by weight. In the case of aerosol preparations, the above percentages relate to the propellent-free preparation.

The following Examples illustrate the invention:

EXAMPLES

1. Trichocosmetic Tests

Shampoos containing quaternary ammonium compounds (QUAT) according to the invention (1.1 and 1.2), comparison shampoos containing known quaternary ammonium compounds (1.3 and 1.4) and a standard shampoo without any quaternary ammonium compounds (1.5) were prepared and subjected to trichocosmetic tests.

The following quaternary ammonium compounds were used:

(1) 2-hydroxyhexadecyl-2-hydroxyethyl dimethylammonium chloride (see Example 3 of U.S. Pat. No. 4,492,802) (corresponds to formula I with $R^1$=n-tetradecyl, $R^2=R^4=CH_3$, $R^3=—CH_2—CH_2—OH$ and $A=Cl^-$)

(2) 2-hydroxyhexadecyl-bis-(2-hydroxyethyl)-methylammonium chloride (corresponds to formula I with $R^1$=n-tetradecyl, $R^2=—CH_3$ and $R^3=R^4=—CH_2—CH_2—OH$ and $A=Cl$)

(3) cetyl trimethylammonium chloride ("Dehyquart" A, a trademark of Henkel KGaA, Federal Republic of Germany)

(4) tallow alkyl-tris-(oligooxyalkyl)-ammonium phosphate ("Dehyquart" SP, a trademark of Henkel KGaA, Federal Republic of Germany). The composition of the shampoos is shown in Table 1.

Measurement of Wet Combability (Laboratory Test)

Standard strands of hair which had been predamaged under defined conditions by bleaching and cold waving were used. They were shampooed in lukewarm water with the shampoos shown in Table 1 and rinsed with clear water. Wet combability was determined by measuring the resistance to combing, i.e. the force required to draw a comb through a lock of hair, using a type 1402 modified tensile testing machine (Zwick Co., Einsingen in Ulm/Danube, Federal Republic of Germany). The test arrangement is described in "Riechstoffe, Aromen, Kosmetika" No. 12, (1977), page 325, columns 2 and 3.

To minimize error, combing resistance was determined 15 times with each of the shampoos to be tested and the average values formed. The average combing resistance values measured were expressed in percent of the standard. The standard was determined after shampooing with test shampoo 1.5 without any quaternary ammonium compounds and rinsing with clear water.

The results of the test are shown in Table 1.

Testing of Trichocosmetic Properties (Salon Test)

The trichocosmetic properties were tested and evaluated on 10 subjects, each having hair of different quality, using the "half-and-half" test. The test was conducted by a trained hairdresser. The half-and-half test is used for the comparative testing of two hair treatment preparations or of one hair treatment preparation and one standard on test subjects.

Shampoos 1.1, 1.2, 1.3 and 1.4 were each compared with the standard shampoo 1.5. The figures quoted in Table 1 are a measure of how much shampoos 1.1 to 1.4 differ from the evaluation of the standard shampoo 1.5, a positive number indicating an improvement.

Procedure and Evaluation

The hair of 10 test subjects was wetted and parted in the middle. With 5 of the test subjects, the standard shampoo 1.5 was applied to the left-hand side and the comparison shampoo to the right-hand side of the head in equal quantities of 5 g (prewashing). With the other 5 test subjects, both sides of the head were treated with the same product. Both sides were shampooed in the same way and rinsed with water. For the main wash, another 2.5 g. of each of the shampoos was applied to the same side of the head, rubbed in and thoroughly rinsed out with clear water.

During and after hair washing, the criteria indicated in the following Table were separately assesed by the hair dresser for each of the two sides of the head. Evaluation was carried out by the awarding of marks (1=excellent, 2=good, 3=moderate, 4=poor). The marks awarded to the 10 test subjects for the same product were converted into average values. The average values for the standard product were subtracted from the average values for the comparison product. The resulting paired differences in the average evaluations of 10 test subjects are shown in Table 1.

TABLE 1

|  | Invention | | Comparison | | |
| --- | --- | --- | --- | --- | --- |
|  | 1.1 % by weight | 1.2 % by weight | 1.3 % by weight | 1.4 % by weight | 1.5 % by weight |
| Test shampoos |  |  |  |  |  |
| Fatty alcohol ($C_{12-14}$) + 2 E.O. sulfate Na salt (28%) (ANIONIC SURFACTANT) | 50 | 50 | 50 | 50 | 50 |
| QUAT 1 (INVENTION) | 2 | — | — | — | — |
| QUAT 2 (INVENTION) | — | 2 | — | — | — |
| "Dehyquart" A (25%) (QUAT) | — | — | 8 | — | — |
| "Dehyquart" SP (50%) (QUAT) | — | — | — | 4 | — |
| Water (fully deionized) | 48 | 48 | 42 | 46 | 50 |
| Laboratory wet combability test (% combing resistance) | 83 | 72 | 88 | 120 | 100 |
| Salon test |  |  |  |  |  |
| Wet Hair |  |  |  |  |  |
| Combability | 0.6 | 0.7 | 0.4 | 0.2 | 0 |
| Feel | 0.6 | 0.7 | 0.1 | 0.1 | 0 |
| Salon test |  |  |  |  |  |
| Dry Hair |  |  |  |  |  |
| Combability | 0.5 | 0.5 | −0.1 | 0 | — |
| Antistatic/chargeability | 0.5 | 0.5 | −0.1 | 0 | — |
| Feel | 0.6 | 1.0 | −0.2 | 0 | — |

TABLE 2

2. Application Examples
2.1 Hair-raising preparations

| Ingredients | Formulation | | |
| --- | --- | --- | --- |
|  | 2.1.1 | 2.1.2 | 2.1.3 |
| QUAT 1 (INVENTION) | 3% by wt. | — | — |
| QUAT 2 (INVENTION) | — | 2.5% by wt. | — |
| QUAT 2 (INVENTION) | — | — | 5% by wt. |
| Sodium chloride | 7% by wt. | 5% by wt. | 5% by wt. |
| Citric Acid | to pH = 6.5 | to pH = 6.5 | to pH = 6.5 |
| Water | ad 100% | ad 100% | ad 100% |
| Viscosity (20° C.) mPa · s | 100 | 100 | 100 |

TABLE 3

2.2 Shampoos

| Ingredients | Formulation | | | | |
| --- | --- | --- | --- | --- | --- |
|  | 2.2.1 % by weight | 2.2.2 % by weight | 2.2.3 % by weight | 2.2.4 % by weight | 2.2.5 % by weight |
| ($C_{12-14}$) fatty alcohol-2 EO-sulfate, Na salt (28%) (ANIONIC SURFACTANT) | 35 | 40 | 50 | — | — |
| ($C_{12-14}$) fatty alcohol sulfate triethanolammonium salt (42%) (ANIONIC SURFACTANT) | — | — | — | 30 | — |
| ($C_{12-14}$) fatty alcohol sulfate monoethanolammonium salt (32%) (ANIONIC SURFACTANT) | — | — | — | — | 30 |
| QUAT 1 (INVENTION) | 1 | — | 1.5 | — | — |
| QUAT 2 (INVENTION) | — | 2.5 | — | 2 | 2 |
| Preservative ("Brinidox" L, a trademark of Henkel Corp. U.S.A. for 5, brosmo-5-nitro-1,3-dioxane,10% solution in propylene glycol) | 0.2 | 0.2 | 0.2 | 0.2 | 0.2 |
| Citric acid to PH = | 6.5 | 6.5 | 6.5 | 6.5 | 6.5 |

TABLE 3-continued

2.2 Shampoos

| Ingredients | Formulation | | | | |
|---|---|---|---|---|---|
| | 2.2.1 % by weight | 2.2.2 % by weight | 2.2.3 % by weight | 2.2.4 % by weight | 2.2.5 % by weight |
| Water (fully deionized) | ad 100% | ad 100% | ad 100% | ad 100% | ad 100% |

We claim:

1. An aqueous shampoo consisting essentially of;
   0.5 to 8% of a hair conditioning compound of the formula

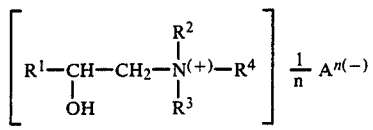

wherein:
$R^1$ is a $C_{12-16}$-n-alkyl;
$R^2$ is a $C_{1-4}$-n-alkyl;
$R^3$ is a $C_{1-4}$-hydroxyalkyl;
$R^4$ is a $C_{1-4}$-n-alkyl or a $C_{2-4}$-hydroxyalkyl;
A is an inorganic or organic acid anion; and
n is the valence of said anion; and
5 to 20% of at least one anionic surfactant of the formula:

$$R^5—O(C_2H_4O)_m—SO_3M$$

wherein:
$R^5$ is a linear $C_{10-18}$-alkyl;
m is 0 or an integer from 1 to 12; and
M is lithium, sodium, potassium, magnesium, ammonium, monoethanolammonium, diethanolammonium, or triethanolammonium;
all weights being based on the weight of the shampoo.

2. An aqueous shampoo consisting essentially of;
   0.5 to 8% of a hair conditioning compound of the formula of claim 1 wherein:
   $R^1$ is a $C_{12-16}$-n-alkyl;
   $R^2$ is methyl;
   $R^3$ is 2-hydroxyethyl;
   $R^4$ is methyl or 2-hydroxyethyl; and
   A is chloride; and
   5 to 20% of at least one anionic surfactant of the formula:

$$R^5—O(C_2H_4O)_m—SO_3M$$

wherein:
$R^5$ is a linear $C_{10-18}$-alkyl;
m is 0 or an integer from 1 to 12; and
M is lithium, sodium, potassium, magnesium, ammonium, monoethanolammonium, diethanolammonium, or triethanolammonium;
all weights being based on the weight of the shampoo.

3. An aqueous shampoo consisting essentially of;
   0.5 to 8% of a hair conditioning compound of the formula 2-hydroxyhexadecyl-2-hydroxyethyl dimethylammonium chloride; and
   5 to 20% of at least one anionic surfactant of the formula:

$$R^5—O(C_2H_4O)_m—SO_3M$$

wherein:
$R^5$ is a linear $C_{10-18}$-alkyl;
m is 0 or an integer from 1 to 12; and
M is lithium, sodium, potassium, magnesium, ammonium, monoethanolammonium, diethanolammonium, or triethanolammonium;
all weights being based on the weight of the shampoo.

4. An aqueous shampoo consisting essentially of;
   0.5 to 8% of a hair conditioning compound of the formula 2-hydroxyhexadecyl-bis-(2-hydroxyethyl)-methylammonium chloride; and
   5 to 20% of at least one anionic surfactant of the formula:

$$R^5—O(C_2H_4O)_m—SO_3M$$

wherein:
$R^5$ is a linear $C_{10-18}$-alkyl;
m is 0 or an integer from 1 to 12; and
M is lithium, sodium, potassium, magnesium, ammonium, monoethanolammonium, diethanolammonium, or triethanolammonium;
all weights being based on the weight of the shampoo.

5. The shampoo of claim 1 wherein said anionic surfactant is substituted up to 50% by weight by an ampholytic or zwitterionic surfactant, or a mixture thereof.

6. The shampoo of claim 5 wherein said ampholytic detergent is at least one N-$C_{8-18}$-alkyl-beta-aminopropionic acid or N-hydroxyethyl-N-cocosacylamidopropyl glycine, and said zwitterionic surfactant is at least one of N-cocosalkyldimethyl glycine or N-cocasacylamidopropyl dimethyl glycine.

7. In an aqueous shampoo comprising at least one surfactant, water, and at least one standard additive selected from the group consisting of thickener, opacifier, pH stabilizer, preservative, dye, perfume, anti-dandruff agent, sebostatic agent, vitamin, or vegetable extract, the improvement wherein
   said surfactant is present in 5 to 20% by weight based on the weight of the shampoo and consists essentially of an anionic surfactant of the formula $$R^5—O(C_2H_4O)_m—SO_3M$$

wherein:
$R^5$ is a linear $C_{10-18}$-alkyl;
m is 0 or an integer from 1 to 12; and
M is a lithium, sodium, potassium, magnesium, ammonium, monoethylammonium, diethylammonium, or triethylammonium ion,
and which anionic surfactant is substituted in 0 to 50% by weight by at least one ampholytic surfactant or zwitterionic surfactant; and
wherein a hair conditioning agent is present in 0.5 to 8% by weight based on the weight of the shampoo, consisting essentially of at least one compound of the formula

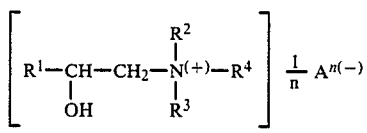

wherein:
$R^1$ is a $C_{12-16}$-n-alkyl;
$R^2$ is a $C_{1-4}$-n-alkyl;
$R^3$ is a $C_{1-4}$-hydroxyalkyl;
$R^4$ is a $C_{1-4}$-n-alkyl or a $C_{2-4}$-hydroxyalkyl;
A is an inorganic or organic acid anion; and
n is the valence of said anion.

8. The shampoo of claim 7 wherein:
$R^1$ is a $C_{12-16}$-n-alkyl;
$R^2$ is methyl;
$R^3$ is 2-hydroxyethyl;
$R^4$ is methyl or 2-hydroxyethyl;
A is chloride;
$R^5$ is a linear $C_{12-14}$-alkyl;
m is 0 or 2; and
M is sodium, monoethanolammonium or triethanolammonium.

9. An aqueous hair rinse preparation consisting essentially of:
0.5 to 10% by weight of a hair conditioning compound of the formula

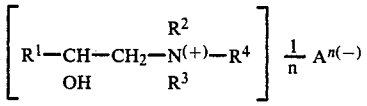

wherein:
$R^1$ is a $C_{12-16}$-n-alkyl;
$R^2$ is a $C_{1-4}$-n-alkyl;
$R^3$ is a $C_{1-4}$-hydroxyalkyl;
$R^4$ is a $C_{1-4}$-n-alkyl or a $C_{2-4}$-hydroxyalkyl;
A is an inorganic or organic acid anion; and
n is the valence of said anion; and
0.1 to 10% by weight of an aqueous solution of at least one salt which a chloride, bromide, sulfate, carbonate, or phosphate of lithium, sodium, potassium, ammonium, or magnesium;
all weights based on the total weight of the rinse.

10. The hair rinse of claim 9 wherein:
$R^1$ is a $C_{12-16}$-n-alkyl;
$R^2$ is methyl;
$R^3$ is 2-hydroxyethyl;
$R^4$ is methyl or 2-hydroxyethyl;
A is chloride; and
said salt is sodium chloride or magnesium chloride.

11. A method for conditioning hair, comprising applying a hair conditioning effective amount of at least one compound of the formula:

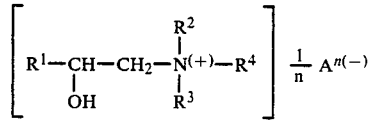

wherein:
$R^1$ is a $C_{12-16}$-n-alkyl;
$R^2$ is a $C_{1-4}$-n-alkyl;
$R^3$ is a $C_{1-4}$-n-hydroxyalkyl;
$R^4$ is a $C_{1-4}$-n-alkyl or a $C_{2-4}$-hydroxyalkyl;
A is an inorganic or organic acid anion; and
n is the valence of said anion.

12. The method of claim 11 wherein said at least one compound is applied as a shampoo.

13. The method of claim 11 wherein said at least one compound is applied as an aqueous hair rinse.

14. The method of claim 11 wherein in said formula,
$R^1$ is a $C_{12-16}$-n-alkyl;
$R^2$ is methyl;
$R^3$ is 2-hydroxyethyl;
$R^4$ is methyl or 2-hydroxyethyl; and
A is chloride.

15. The method of claim 11 wherein said compound is 2-hydroxyhexadecyl-2-hydroxyethyl dimethylammonium chloride.

16. The method of claim 11 wherein said compound is 2-hydroxyhexadecyl-bis-(2-hydroxyethyl)-methylammonium chloride.

* * * * *